US007645137B2

(12) United States Patent
Wasyluch

(10) Patent No.: US 7,645,137 B2
(45) Date of Patent: Jan. 12, 2010

(54) METHOD AND APPARATUS FOR BLEACHING TEETH

(76) Inventor: Bryan Wasyluch, 4191 Dixie Canyon, No. 2, Sherman Oaks, CA (US) 91423

( * ) Notice: Subject to any disclaimer, the term of this patent is extended or adjusted under 35 U.S.C. 154(b) by 591 days.

(21) Appl. No.: 10/309,831

(22) Filed: Dec. 4, 2002

(65) Prior Publication Data

US 2004/0110111 A1 Jun. 10, 2004

(51) Int. Cl.
*A61C 3/00* (2006.01)
*A61C 5/00* (2006.01)

(52) U.S. Cl. ........................................ 433/29; 433/215

(58) Field of Classification Search .................. 433/29, 433/37–39, 80, 34, 42, 215–216

See application file for complete search history.

(56) References Cited

U.S. PATENT DOCUMENTS 5,316,473 A * 5/1994 Hare .......................... 433/29
5,403,578 A * 4/1995 Gordon ...................... 424/53
5,718,577 A * 2/1998 Oxman et al. ................ 433/37
6,435,873 B1 * 8/2002 Burgio ...................... 433/80
6,616,447 B1 * 9/2003 Rizoiu et al. ................ 433/29

* cited by examiner

*Primary Examiner*—John J Wilson
(74) *Attorney, Agent, or Firm*—Gifford, Krass, Sprinkle, Anderson & Citkowski, P.C.

(57) ABSTRACT

A method and apparatus for whitening teeth which allow the user to undergo dental bleaching with the mouth closed and without protruding instruments, trays or electrical wires and the like. The apparatus includes a support structure and a dental whitening composition in contact with the support structure. A light source is included in the apparatus, disposed on or in the support structure so that light emitted from the source contacts on the dental whitening composition. The apparatus has a volume ranging between 0.5-450 $cm^3$ permitting the apparatus to fit entirely within the mouth of a user during treatment.

2 Claims, 5 Drawing Sheets

METHOD AND APPARATUS FOR BLEACHING TEETH

FIELD OF THE INVENTION

This invention relates to methods and apparatus for dental bleaching. In particular the invention relates to methods and apparatus for light accelerated dental bleaching which permit the patient to close the mouth during treatment.

BACKGROUND OF THE INVENTION

Dental bleaching is an increasingly popular treatment and dentists are constantly searching for techniques that are both convenient and comfortable for their patients. Numerous methods and tools have been developed for the purpose of dental bleaching. Typically, a composition containing hydrogen peroxide is applied to the teeth and allowed to remain in contact with the surface to be bleached. Unfortunately, home treatments usually involve long treatment protocols due to the low strength compositions available for home use. For example, a typical treatment regimen may require twice daily 15-30 minute applications of a hydrogen peroxide, or 1-2 hour daily applications of carbamide peroxide, over a period of several weeks.

Alternatively, patients are treated in a dentist's office for more intensive treatment using concentrated bleaching compositions. Disadvantages of these treatments include the inconvenience of remaining in the dental office, often with uncomfortable clamps, dams and retractors affixed to the mouth to keep it in the proper position. Not surprisingly, much effort has been expended in the search for methods of increasing the comfort, convenience and speed of the bleaching process. Various methods and devices have been developed to this end, broadly including those that expose a whitening composition to heat, light or a combination of these. However, such methods and devices require that a user remain in one place with the mouth open, or attached to a heater or light source that extends from the mouth. Thus, there exists a need for methods and apparatus for bleaching teeth that accelerate treatment, allow the patient to move freely during treatment, and avoid the inconvenience of having any part of the treatment apparatus protruding from the mouth.

SUMMARY OF THE INVENTION

A dental apparatus is provided including a support structure adapted to be placed entirely within a user's mouth, a dental whitening composition in contact with the support structure, and a light source disposed on or in the support structure such that light emitted from the source impinges on the dental whitening composition. The apparatus has a volume ranging between 0.5-450 $cm^3$.

The dental whitening composition includes an oxidizing agent which is optionally a peroxide. The composition may be supplied in the form of a gel, emulsion, gum, putty, liquid, paste or a microencapsulated form such as agar gel beads, liposomes and niosomes.

The light source may be a luminescent material such as a phosphorescent, chemiluminescent or phosphorescent substance or a combination of these. The light source may also be a diode, such as light emitting diode or laser diode or a combination of a diode and a luminescent material. Optionally, the light source is in the form of a gel, gum, emulsion, putty, glow tube, glow stick, liquid, varnish, powder, crystalline solid, pellet, aggregate, curable resin or paste.

The support structure may take any of various forms including a dental strip or a dental tray. Optionally, the support structure includes a reflective material disposed on the structure such that light is reflected toward the whitening composition.

A method is provided for treating a dental surface of a user which include the steps of providing a dental apparatus that has a support structure adapted to be placed entirely within the user's mouth, a dental whitening composition in contact with the support structure, and a light source disposed on or in the support structure such that light emitted from the source impinges on the dental whitening composition. The apparatus has a volume between 0.5-450 $cm^3$. In another step included in the method, the light source is activated so that light is emitted by the light source. The apparatus is placed entirely within the user's mouth and then the dental surface to be treated is exposed to the light emitted by the light source thereby treating the dental surface.

DETAILED DESCRIPTION OF THE INVENTION

Dental Apparatus

Figure 1A:
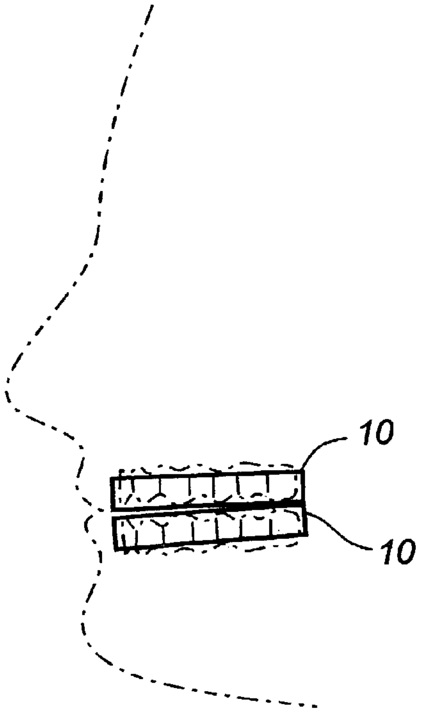
FIG. 1A is a drawing illustrating a side view of an embodiment of an inventive apparatus in place inside a user's mouth.

An apparatus according to the present invention includes a support structure, a dental whitening composition, and a light source. The apparatus is adapted to be contained entirely within the closed mouth of a user, such that the apparatus operates to whiten teeth in the closed mouth of a user without any part of the apparatus protruding from the mouth. This allows the user to rest comfortably while receiving the benefits of dental whitening. FIGS. 1A and 2 illustrate embodiments of the apparatus 10 in place in a user's mouth.

Support Structure

Form of a Support Structure

Figure 1B:
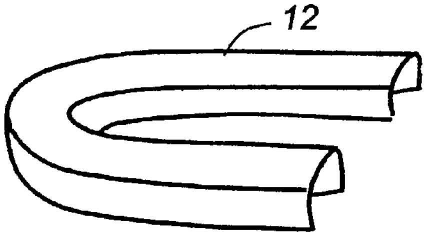
FIG. 1B is a drawing illustrating a perspective view of an inventive apparatus.

The support structure may have any of various forms determined according to the form of whitening composition used, choice of dental surface to be treated, the number of dental treatments to be performed and the length of time over which a single dental treatment is performed. Support structures for dental treatment are known in the art and illustratively include a strip of sheet material and a shaped dental tray approximating the shape of a tooth, part or all of a dental arch or both dental arches. A typical dental tray has a U-shape in order to fit the average dental arch and channels are formed therein for insertion of the teeth during treatment. FIG. 1A illustrates an embodiment of the apparatus 10 in place in a user's mouth wherein the support structure has the form of a dental tray. FIG. 1B illustrates a U-shaped support structure 12.

Figure 2A:
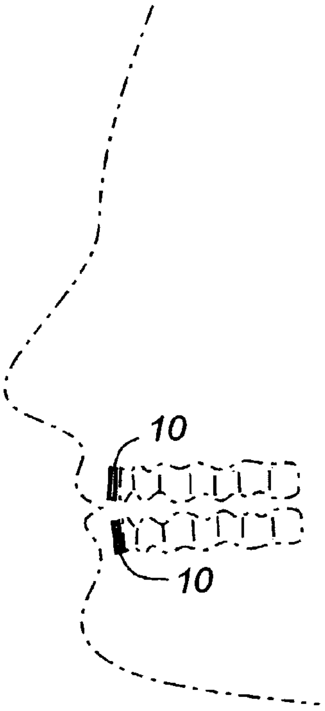
FIG. 2A is a drawing illustrating a side view of an embodiment of an inventive apparatus in place inside a user's mouth.

Particularly preferred is a support in the form of a tape or strip. FIG. 2A illustrates an embodiment of the apparatus 10 in place in a user's mouth wherein the support structure has the form of a sheet material. Further, support structures of the type useful in the present invention are those fabricated to conform to an individual's dentition, as is commonly performed in making dental tools such as bite splints, dental trays for medication delivery etc. The support may be formed to contain, cover or adhere to one tooth or multiple teeth at a time, and one or multiple surfaces of the teeth, such as front and back. This support allows selective treatment, such as treatment of front and back surfaces of front teeth only or treatment of all teeth, as desired. Supports in tape or strip form are known in the art, such as those described in, for example, U.S. Pat. Nos. 5,891,453; 5,894,017; 5,989,569 and 6,045,811.

In one embodiment, the support structure includes a reflective material disposed in or on the support structure so as to direct light toward the tooth surface to be whitened. Exemplary reflective materials include a white or silver coating, a metallic surface, metallic particles or metallic insert, so as to direct light toward the tooth surface to be whitened.

A support structure may have one or more textured surfaces. A textured surface promotes the adherence of the structure to the dentition and promotes contact between the whitening composition and the dental surface to be treated. A textured may include bumps or protrusions in a regular or irregular pattern. Generation of a textured surface is by methods known in the art, illustratively including embossing.

Figure 2B:
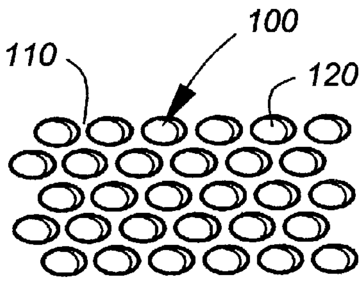
FIG. 2B is a drawing illustrating a textured surface of a support structure.
Figure 2D:
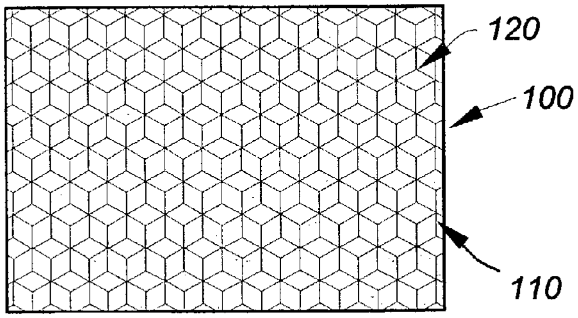
FIG. 2D is a drawing illustrating a textured surface of a support structure.
Figure 2C:
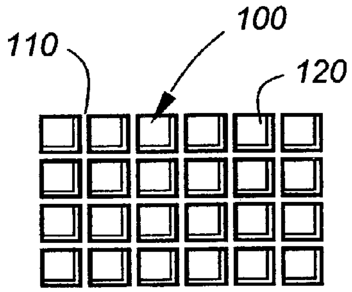
FIG. 2C is a drawing illustrating a textured surface of a support structure.
Figure 2E:
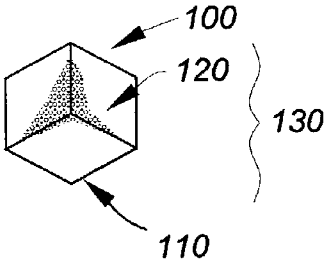
FIG. 2E is a drawing illustrating an individual cell included in a textured surface of a support structure.
Figure 2G:
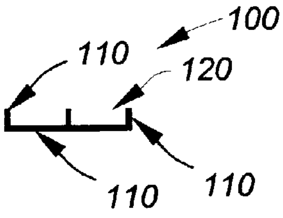
FIG. 2G is a drawing illustrating a cross-section of a textured surface of a support structure.
Figure 2F:
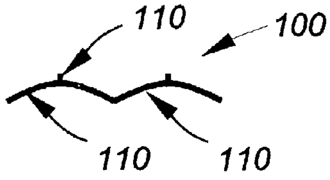
FIG. 2F is a drawing illustrating a cross-section of a textured surface of a support structure.

Optionally, a support structure includes a reservoir for holding whitening composition to be delivered to the dental surface to be treated. For example, a reservoir may be a textured surface that includes a pattern of shaped individual cells in the support structure surface. Each cell includes a wall defining a shape of the cell, and a central depression. The individual cell may have any shape including a geometric shape such as a circle, oval, a polygon, illustratively including a square, rectangle, triangle hexagon or other regular or irregular shape. Cells included in a support structure may all have the same shape and same size or cells may differ depending on such factors as, for example, the viscosity of the composition used and the dental surface to be treated. Examples are shown in FIGS. 2B, 2C and 2D, illustrating shaped cells 100, each having a wall 110 and a central depression 120. Typically, an individual cell has a diameter (or a largest dimension) 130 that ranges in length from about 0.1 to 15 millimeters. A central depression 120 ranges in depth from about 0.1 to 4 millimeters. In a preferred embodiment, the cell is hexagon shaped, forming a honeycomb pattern on a surface of the support structure. An example of a preferred hexagonal pattern is shown in FIG. 2D. The hexagonal cells forming the honeycomb pattern may all have the same size or may differ in size. In a preferred embodiment, an individual hexagonal cell, as shown in FIG. 2E, has 6 sides of equal length, a diameter 130 ranging from about 5 to 6 millimeters and a central depression 120 having a maximal depth of about 0.1 to 4, preferably 2.0, millimeters.

A wall 110 of an individual cell 100 divides one cell from another and defines the central depression 120. A wall 110 may slope towards the central depression 120, as shown in cross-section in FIG. 2F, or a wall 110 may have straight sides as shown in cross-section in FIG. 2G.

Composition of a Support Structure

The support structure may be made of any of the typical biocompatible materials used in forming dental apparatus. Resins, plastics, waxes and the like may be used to form sheet material or a suitable shape by known methods such as injection molding or casting. Thermoset and photocurable materials may be used, particularly for support structures formed to the individual's dentition, as is known in the art. Illustrative examples of synthetic polymers used include polyurethanes, polyvinyl chlorides, acrylates, including ethyl vinyl acrylate, polycarbonate, polyphenylene oxide, polyimide, polyethylene, polypropylene, polystyrene, polyvinyl chlorides, polyamides and polyesters, acetates including ethyl vinyl acetate, combinations thereof and art recognized equivalents. Natural materials may also be used, including natural waxes, plant fiber materials such as cellulose, and the like. Preferred materials include beeswax and paraffin. Further, mixtures of such materials may be used.

For example, a preferred support composition includes paraffin or beeswax. A support in the form of a paraffin or beeswax sheet is moldable such that a dental tray is formed by application of the sheet material to the dentition. Advantageously, a moldable material allows formation of a custom fit dental tray in minutes or less, in some cases almost instantly.

The finished support may have a relatively supple consistency such as a gel, foam or wax such that teeth are not damaged by contact therewith. In a preferred embodiment a support structure is has a gel-like consistency. A gel-like support structure may be formed from materials including exemplary materials such as gelatin, silicone, gelled mineral oils, and the like. Further, materials such as the Versagel C or M series (Penrenco) or other di-block, tri-block, multi-block and radial block copolymers such as the Kraton G series polymers (Shell Chemical) are suitable for use in the invention. Other exemplary materials that may be used include gelled Permethyl 99A-750, 99A-753-59, and 99A-753-58 triblock and starburst polymer mixture, OS129880, OS 129881 and OS 129883 from Lubrizol (a styrene/methacrylate copolymer), Viscogel by Laviosa Chimica Mineraria, silicone products such as Medical Adhesive A, 7-9800, RTB 700,732,736 by Dow Corning and dimethicone copolyols such as Dow Corning 3225C and lauryl methicones such as Dow Corning Q2-5200 all by Dow Corning Company.

Advantageously, the support may include an adhesive for promoting adherence to the dental surface.

Dental Whitening Composition

Dental Whitening Composition Ingredients

A dental whitening composition used in an inventive apparatus includes an oxidizing agent. Oxidizing agents used in dental whitening are known in the art and include, for example, a peroxide, an alkali metal percarbonate, an alkali metal perborate or a combination thereof are illustrative of useful oxidizing agents. Most commonly used peroxides include hydrogen peroxide, carbamide peroxide and alkali metal peroxides.

Concentrations of oxidizing agents as used in dental whitening are known in the art and depend on the circumstances of use as detailed in, for example, U.S. Pat. Nos. 5,032,178; 5,409,631; 5,785,527; 6,149,895; 6,155,832; 6,162,055; 6,165,448; 6,231,343; 6,306,370; 6,309,625; 6,312,666; 6,343,933; 6,387,353; 6,440,396; and 6,458,340. A peroxide is typically used at concentrations ranging from 1% to 50%. Typically, lower concentrations of hydrogen peroxide, from 2-10% are made available to patients for in home use. Higher concentrations are used in a clinician's office, ranging from 10-35%.

The dental whitening composition may further include optional ingredients such as a buffer, a thickener or gelling agent, a solvent, a surfactant, additives such as flavoring agents or preservatives and other inert customary ingredients as detailed in, for example, U.S. patents referenced above. A further ingredient of the dental whitening composition is an optional heat or light absorbing component or a reaction accelerator such as a catalyst as detailed in, for example, U.S. Pat. Nos. 6,287,120; 6,439,888 and 6,440,396.

A dental composition may also contain a therapeutic agent such as an agent to treat dental or systemic diseases or conditions, including anti-plaque agents, anesthetics, desensitizing agents, analgesics, antibiotics, antifungals, antirmicrobials, antivirals, anti-inflammatory agents, steroids, remineralizing agents, and anticarciogenic agents.

Form of a Dental Whitening Composition

The dental whitening composition may be applied to a support and/or to the dental surface to be whitened. The composition may have any of various forms, illustratively including liquid, gel, emulsion, putty or paste. The composition may further be in a microencapsulated form such as alginate beads or agar gel beads, liposomes, niosomes, or other form in which a boundary layer is formed to surround the whitening composition. Such formulations are known in the art, for example as taught in U.S. Pat. Nos. 6,375,985; 6375,968; 6,319,507; 6,217,908 and Microencapsulation: Methods and Industrial Applications in Drugs and the Pharmaceutical Sciences, Vol. 73; S. Benita (Ed.); Marcel Dekker; 1996. A time-release formulation is also contemplated, such as that disclosed in U.S. Pat. No. 6,197,331, for example.

A dental whitening composition may be conveniently packaged so as to deliver an amount appropriate for a single use. A single use amount will depend on the whitening composition used, the area of the dental surface to be treated and the amount of whitening desired. Generally, a single use amount will range from 0.1-1 or less ml for smaller treatment areas, and between about 2 ml to 5 ml for larger areas. Larger amounts, ranging from 6 ml to 15 ml or even larger, may be appropriate in some cases, such as where all an individual's teeth are to be whitened at once. Packaging of amounts appropriate for a single use are known in the art, for example, including pillow packs and the like.

Disposition of a Whitening Composition in Relation to a Support Structure

A whitening composition may be applied to, or incorporated in, a support structure so that when the apparatus is placed in the user's mouth, the whitening composition contacts a dental surface to be whitened.

In one embodiment, the whitening composition is incorporated in the support structure from which it is extruded or leeches onto the dental surface while the patient wears the apparatus. For example, carbamide peroxide may be included in a support structure composed of an anhydrous gel such that when the support is placed in the mouth of a user, the carbamide peroxide leeches from the gel into the aqueous environment of the dental surface. In another example, a tape or strip support structure may be coated with a layer of whitening composition. Whitening composition may be applied to the support structure at anytime, such as during manufacture, or just prior to use. In another example, a tape or strip may contain microencapsulated gel-like beads containing hydrogen peroxide. This strip may be cut or separated at the desired length and applied to the tooth surface.

In a preferred embodiment, a whitening composition in the form of hydrogen peroxide microencapsulated in gel-like beads, such as alginate beads, is applied to a moldable support structure having a honeycomb textured surface. The moldable support structure is composed of a pliant material such as wax or other material which readily conforms to the shape of the teeth. The support material may be molded by hand at room temperature or rendered moldable by application of heat. This combination has excellent delivery properties due in part to the close adaptation of the honeycomb shapes on the support surface to the smoother surface of the teeth which may be aided by Van der Walls forces between these surfaces. In use, the encapsulated whitening agent is released by application of pressure, heat or light.

Light Sources

Light sources and wavelengths of light providing energy that promotes activation of dental whitening compositions are known in the art. For example, see U.S. Pat. Nos. 4,661,070; 4,952,143; 5,032,178; 5,658,148; 5,713,738; 5,785,527; 6,056,548; 6,106,293; 6,149,895; 6,155,832; 6,162,055; 6,231,343; 6,287,120; 6,361,320; 6,416,319. In the context of the present invention, any light source may be used which can be incorporated into the apparatus such that the apparatus operates to whiten teeth in the closed mouth of a user without any protruding parts.

A light source may be a luminescent source, such as fluorescent, phosphorescent or chemiluminescent. Other exemplary light sources include light emitting diodes and laser diodes. These light sources are powered in a manner such that the light is emitted in the mouth without external connections to a power source. For example, light emitting diodes and laser diodes operable in the present invention may be powered by an energy storage device such, as a battery or capacitor, incorporated into the apparatus. A chemiluminescent source is powered by mixing appropriate chemical reactants so that a light producing reaction occurs during treatment. A fluorescent or phosphorescent source included in the apparatus is powered by exposure to exciting light so that fluorescent or phosphorescent light is emitted during dental treatment. For example, a phosphorescent source may be held under exciting light for a period of time before placement in the patient's mouth for dental treatment. Alternatively, a phosphorescent source may be placed in the patient's mouth and subsequently exposed to exciting light while the patient's mouth is open. The phosphorescent afterglow then continues to activate the whitening compound after the patient closes the mouth.

Combinations of light sources are specifically contemplated as within the scope of the invention. For example, a fluorescent source may be used in conjunction with a second light source, such as a phosphorescent light such that the fluorescent source is excited by the emitted phosphorescent light. Similarly, combinations of diode sources and phosphorescent or fluorescent sources may be used.

Chemiluminescent Light Sources

A chemiluminescent light source refers to light produced by a chemical reaction. Different colors of chemiluminescent light, illustratively including blue, green and yellow, are produced according to the different chemical reactants. Examples of chemiluminescent light reactants and systems are found in U.S. Pat. Nos. 3,391,068; 3,511,612; 3,539,794; 3,557,233; 3,576,987; 3,584,211; 3,597,362; 3,654,525; 3,749,620; 3,752,406; 3,775,336; 3,800,132; 3,808,414; 3,888,786; 3,940,604; 3,974,368; 4,064,428; 4,313,843; 4,751,616; and 4,717,511.

Components of one type of chemiluminescent reaction include an oxalate component, an activator component and a fluorophore. Illustrative examples of an oxalate component include a phenyl oxalate ester such as dibutyl phthalate, bis (2,4,5-trichloro-6-carbopentexyphenyl) oxalate, bis(2,4-dinitrophenyl)oxalate (DNPO) and bis(2,4,6-trichlorophenyl)oxalate. Illustrative examples of an activator include dimethyl phthalate, t-butyl alcohol, hydrogen peroxide and sodium salicylate. Examples of fluorophores used in chemiluminescent reactions include 1-chloro-9,10-bis(phenylethynyl)anthracene, 9,10-diphenylanthracene, Rhodamine B, 5,12-Bis(phenylethynyl)-naphthacene and tetraphenylnaphthacene. Further chemiluminescent systems may be based on dioxetanes, luminols, acridinium esters and aryloxalates, as described in H. Akhavan-Tafti, et al., Chemiluminescent Haloalkoxy-substituted Dioxetanes: Properties and Applications, in *Bioluminescence and Chemiluminescence Molecular Reporting with Photons*, J. W. Hastings, L. Kricka and P. Stanley, Eds., John Wiley and Sons, Chichester, 497-500 (1997) and Bioluminescence and Chemiluminescence: Progress and Current Applications Robinson by Phillip E. Stanley (Editor), Larry J. Kricka (Editor), World Scientific Pub Co; 2002. Other chemiluminescent light sources include bioluminescent systems such as those taught in U.S. Pat. No. 5,876,995.

Components of chemiluminescence reactions are provided in separate containers and the components combined when chemiluminescent light production is desired. Glow sticks and glow tubes are examples of available commercial packaging for chemiluminescent materials. Typically, such packaging includes a breakable multi-compartment internal container, each enclosing a chemical reactant or stable mixture of selected reactants. The internal containers are surrounded by an outer container such that by breaking the internal containers, the reactants are mixed and held within the outer container. For example, a phenyl oxalate ester and a fluorophore may be stored together in one compartment, and hydrogen peroxide in another compartment, the compartments broken in order to mix the reactants and produce light.

In another embodiment, an oxalate compound and a fluorophore may be stored together in one inner compartment, and a hydrogen peroxide containing composition is present within the outer container, such that the inner compartments broken in order to mix the reactants within the outer container and produce light. The contents of this container may then be applied to a support or dental surface as a light source. Additionally, it will be appreciated that the hydrogen peroxide present in a light source of this type is also a whitening composition.

In one embodiment, a chemiluminescent light source is provided in microencapsulated form. Reaction components are separately incorporated into microcapsules, such as alginate beads. Components are mixed by placing reaction component containing beads in proximity and releasing the components from the beads by application of pressure, dissolution of the capsule barrier, warming or similar release methods known in the art, such that the components react and produce light. For example, in accordance with the invention, an oxalate compound and a fluorophore may be stored microencapsulated together, and hydrogen peroxide microencapsulated separately. These two forms of microcapsules are applied to a support, such as a honeycomb textured moldable sheet, or directly to a dental surface. A chemiluminescent reaction may then be initiated by releasing the reaction components from the microcapsules. The reaction components are thus mixed, initiating the chemiluminescent reaction and producing light. One of skill in the art will recognize that other combinations of chemiluminescent reactants are operable in this embodiment. It is appreciated that a hydrogen peroxide solution used in this context as a component of a chemiluminescent reaction, is also a whitening composition component.

In another embodiment, one component of a chemiluminescence reaction may be microencapsulated and other reactants provided in another form. The microspheres are permeabilized so that the reactants contained therein are released into contact with the other reactants, allowing the chemiluminescent reaction to occur. For example, microspheres containing an oxalate compound and a fluorophore may be applied to a support, such as a honeycomb textured moldable sheet, or directly to a dental surface. A hydrogen peroxide containing liquid, gel, emulsion, putty, paste or the like is also applied to the support or dental surface. The microencapsulated components are released, by application of pressure, enzymatic or solvent mediated dissolution of the capsule barrier, warming or similar release methods known in the art. Released microencapsulated components then react with the other reaction components so that a chemiluminescent reaction occurs. One of skill in the art will recognize that other combinations of chemiluminescent reactants are operable in this embodiment. It is appreciated that a hydrogen peroxide solution used in this context as a component of a chemi luminescent reaction, is also a whitening composition component.

In a further embodiment, as described above, one component of a chemiluminescence reaction may be microencapsulated and other reactants provided in another form, such as a solution. In this case, the microspheres are made permeable to a molecules of selected size, in order to allow other reactants to diffuse into the microsperes but preventing release of microencapsulated components. The interaction of the reaction components initiates a light producing reaction inside the microsphers. For example, microspheres containing an oxalate compound and a fluorophore may be applied to a support, such as a honeycomb textured moldable sheet, or directly to a dental surface followed with a hydrogen peroxide containing liquid, gel, emulsion, putty or paste. In this case, the microspheres are made permeable to molecules of selected size, in order to allow hydrogen peroxide to diffuse into the microspheres but not allowing release of the oxalate compound and fluorophore. One of skill in the art will recognize that other combinations of chemiluminescent reactants are operable in this embodiment. It is appreciated that a hydrogen peroxide solution used in this context as a component of a chemiluminescent reaction, is also a whitening composition component.

It will be evident to one of skill in the art that separately packaged chemiluminescence reaction components may be mixed to initiate the light producing reaction before application to a support or dental surface if desired. For example, chemiluminescent reaction components may be packaged in separate compartments within in a dispensing device such as a plastic bottle or tube. The barrier between the separate compartments may be broken by pressure, heat or the like, and the reactants mixed to initiate the chemiluminescence reaction within the dispensing device. The light producing reaction mixture, in the form of a liquid, gel or the like, may then be dispensed onto the support or the dental surface as desired.

Phosphorescent Light Sources

Phosphorescent materials are those which are excited by UW or visible light, resulting in the emission of light that lasts after the exposure to the exciting light has ceased. Duration of the emission is typically from minutes to hours, but can even extend for several days. Many useful phosphorescent materials occur naturally or have been developed, including both inorganic and organic compounds.

Common inorganic phosphorescent materials suitable for use as a light source in the present invention include a metal cation, a non-metal anion and an "activator". Examples of suitable inorganic phosphors include sulfides, metal aluminate oxides, silicates and various rare earth compounds. For instance, as is known in the art, ZnS and ZnS may be combined with various activators such as aluminum, cerium, copper, europium, gadolinium, gallium, gold, indium, lead, manganese, praseodymium, samarium, scandium, silver, terbium, and other rare earth elements and halogens to produce a phosphorescent material, and these may be used as a light sources in the invention. Further examples of sulfide phosphors illustratively include alpha barium-zinc sulfides, barium-zinc-cadmium sulfides, CaS:Bi, CaSrS:Bi, strontium sulfides, ZnCdS:Cu and ZnCdS:Ag. Metal aluminate oxides include alkaline earth aluminate oxides, such as strontium aluminum oxide, calcium aluminum oxide and barium aluminum oxide. Strontium aluminate with a europium activator ($SrAlO_3$:Eu) is an exemplary phosphoresecent material suitable for use as a light source in an inventive apparatus. Further oxide phosphorescent materials that illustrate phosphorescent materials that may be used as a light source in the invention include aluminum oxides, boric oxides, calcium oxides, dysprosium oxides, europium oxides and strontium oxides. Further examples of phosphorescent materials include those taught in U.S. Pat. Nos. 3,595,804; 3,957,678; 3,970,582, 5,376,303, 5,424,006, 5,558,817 and 5853614. Examples of phosphorescent organic materials are found in U.S. Pat. Nos. 5,229,16 and 5,618,467. Any of these listed phosphorescent materials, mixtures thereof, and art recognized equivalents may be used as a light source in an apparatus according to the present invention.

Preferred phosphorescent light sources are those having long-lasting light emission. For example, strontium aluminate with a europium activator ($SrAlO_3$:Eu) is a suitable long-lasting emitter, having an emission time of about 10 hours following exposure to exciting light.

Phosphorescent materials suitable for use in an inventive apparatus are commercially available, illustratively including those manufactured and sold under the brand name Picariko by Chemitech, Inc., Tokyo and available from F. W. Bass International; those made by Nemoto & Company, Tokyo and available from United Mineral & Chemical Corporation, Lyndhurst, N.J. under the brand name LumiNova. Further, PermaglowR products by Chemitech Inc., Tokyo such as Natural Blue color, having a peak emission at 489, produced as particles having 30-65 micron size is a suitable phosphorescent material used as a light source in an inventive apparatus. Sizes outside this range may also be workable.

Fluorescent Light Sources

Fluorescent light sources suitable for use in an inventive apparatus illustratively include such compounds as the commercially available coumarin dyes such as Fluorescent Yellow FP, Macrolex Fluorescent Yellow 10GN, and Fluorescent Red G, (Bayer); Thermoplast Yellow 084 (BASF), and Solvent Orange 63, HOSTASOL Solvent Yellow 98, and Vat Red 41, (Clariant Corp.) and LUMOGEN F Dyes manufactured by BASF Corporation as well as art recognized equivalents.

Diode Light Sources

Diode light sources suitable for use in an inventive apparatus include both light emitting diodes and laser diodes. Diodes and methods of their incorporation into a support structure for use in an internal body cavity are known in the art and includes those described in U.S. Pat. Nos. 5,500,009; 5,702,432; 5,989,245; 6,077,073 and 6,439,888. Of particular interest are individual diodes and diode arrays that are incorporated into a support structure along with a power source, see for example, U.S. Pat. No. 5,445,608.

Disposition of a Light Source in Relation to a Support Structure

A light source may be disposed on and/or in the support structure so that light emitted from the light source impinges on the whitening composition.

Figure 3A:
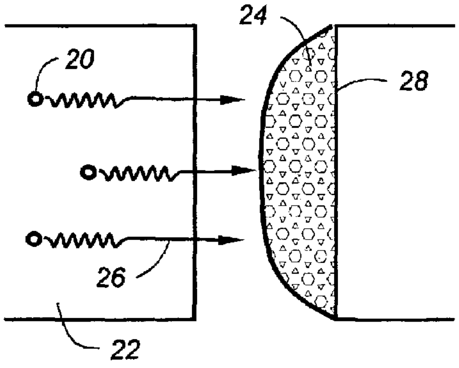
FIG. 3A is a drawing illustrating an embodiment of an inventive apparatus.

In another embodiment, a light source is made integral to the support by being included in a material forming the support structure. In an embodiment shown in FIG. 3A, a luminescent material light source 20 is integral to the support structure 22. Also shown is a dental whitening composition 24 which is contacted by light 26 emitted by the light source 20. The dental whitening composition is shown in contact with a dental surface 28. Methods and compositions for forming luminescent articles by including a luminescent material in a resin, plastic, wax, sheet material or other support structure forming material are known in the art, for example, as described in U.S. Pat. Nos. 3,796,668; 4,211,813; 4,629,583; 4,707,297; 4,911,830; 5,464,651; 5,618,467; 5,783,108; 5,914,076 and 6,375,864.

Figure 3B:
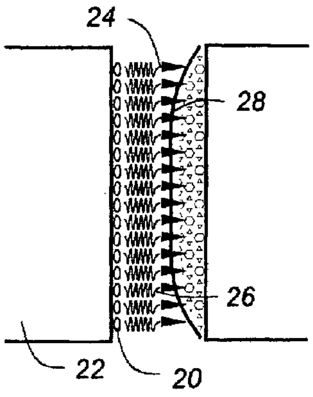
FIG. 3B is a drawing illustrating an embodiment of an inventive apparatus.
Figure 3C:
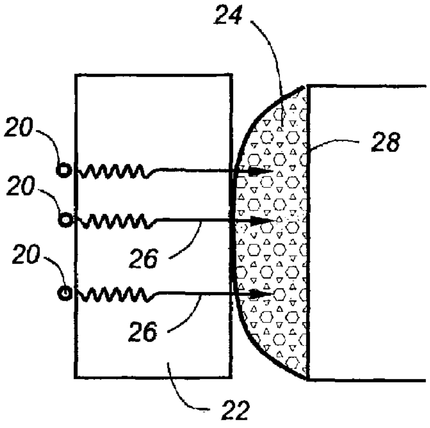
FIG. 3C is a drawing illustrating an embodiment of an inventive apparatus.

Alternatively, a diode or luminescent material may be disposed on an external surface of a support. In an embodiment shown in FIG. 3B, a light source 20 is present on an external surface of a support structure 22. Also shown is a dental whitening composition 24 which is contacted by light 26 emitted by the light source 20. The dental whitening composition is shown in contact with a dental surface 28. FIG. 3C illustrates an arrangement wherein the light source 20 is on a surface of the support structure 22 distal to the dental surface 28 which is in contact with the whitening composition 24. A light source disposed on a support structure may have various forms illustratively including a diode and a luminescent material in the form of a gel, gum, emulsion, putty, liquid paint, varnish, curable resin, wax, tape, glow tube, glow stick or paste which can be applied to a support. Methods and compositions for such luminescent compositions are known in the art and are disclosed herein.

A diode and its power source may be applied to a support structure surface by conventional methods illustratively including adhesive fixation. Similarly, a luminescent light source in may be affixed to a support using an adhesive. Suitable adhesives and their use are known in the art and preferably include food grade adhesives such as Spectrum 0172, available from the Velcro Group Corporation, and those materials disclosed in U.S. Pat. Nos. 3,527,646; 4,504,502; 4,910,031; 4,913,919; 4,981,707; 5,275,830; 5,275,831 and 5,298,268.

Optionally, a protective material covers the light source and/or whitening composition. For example, a layer of a sheet material, such as polypropylene, polyvinylidene chloride, polyethylene and the like, is placed over the light source and/or whitening composition. The protective material may be placed over a whitening composition for instance where the composition is applied to the support in advance of use, such as during manufacture, so as to protect the composition from dehydration, exposure to light, air and the like. The protective material may then be removed just prior to use.

Similarly, an optional protective material may be disposed so as to cover a light source in order to aid in securing in the light source to the support and to protect the light source from the environment. In one embodiment, a light source includes a phosphorescent powder affixed to a surface of a moldable sheet material support structure using an adhesive. Optionally, a protective sheet material is affixed to the same surface of the support structure after application of the phosphorescent powder. The protective sheet material aids in keeping the phosphorescent powder in place on the support and protects the powder from exposure to the environment. The protective sheet material may be translucent to allow excitation of the light source and/or emission of the phosphorescent light.

A light source may be disposed on, integral to, or in a support structure in multiple forms in an inventive apparatus. For instance, a light source may be incorporated in a material included in or forming the support structure. In addition, a light source may be applied to the support structure.

Advantageously, a light source may be disposed in relation to the support such that only teeth to be treated are exposed to the light. For example, a light source in the form of a gel may be placed in proximity to a subset of teeth. Similarly, a diode source may be positioned where desired on a support such that light is directed primarily a certain tooth or dental surface to be treated.

Further, a light source may be placed so that multiple surfaces of a tooth may be treated simultaneously. For example, a support incorporating a luminescent substance may be formed to fit the individual's dentition so that both the front and back surfaces of a tooth are exposed to a whitening compound and activating light. No known light-activated system allows for simultaneous light accelerated whitening of the front and back of a tooth with no protruding parts (i.e., with the mouth closed).

A luminescent material or diode may be partially or wholly surrounded by support structure material such that light is transmitted through the support structure to the dental whitening composition. In one embodiment of this arrangement (not shown), a chemiluminescent light source may be located in an interior chamber of the support structure such as a fluid-tight internal cavity for a chemical reactant. The internal cavity is sub-divided into at least two compartments, each containing a chemical reactant. The compartments are separated by an internal divider which can be broken so as to mix the chemical reactants such that a chemiluminescent reaction occurs, producing light.

Figure 3D:
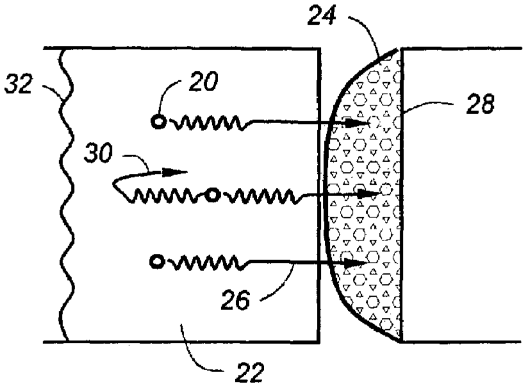
FIG. 3D is a drawing illustrating an embodiment of an inventive apparatus.

In an embodiment shown in FIG. 3D, a light source 20 is integral to support structure 22. The light source 20 emits light 26 which travels toward the dental whitening composition 24 as well as light 30 traveling in other directions. A reflective material 32 included in the apparatus 40 directs light 31 toward the whitening composition.

Size of Dental Apparatus

The dental apparatus is sized to fit entirely within the mouth of a patient while the patient undergoing dental whitening. Thus, the support structure, whitening composition and light source are in place and operable while the patient's mouth is closed. Further, because it is not necessary to attach the apparatus to an external power source during treatment, the patient can move freely and go about normal activities without any wires, fibers, batteries or other connections, such as to a power or light source, protruding or extending outside the mouth in the course of treatment. Typical size of an apparatus is ranges from about 0.5 $cm^3$ to about 450 $cm^3$ and is less than the volume of an average adult human oral cavity which ranges from about 100 to 500 $cm^3$.

Method of Treating a Dental Surface

Figure 4A:
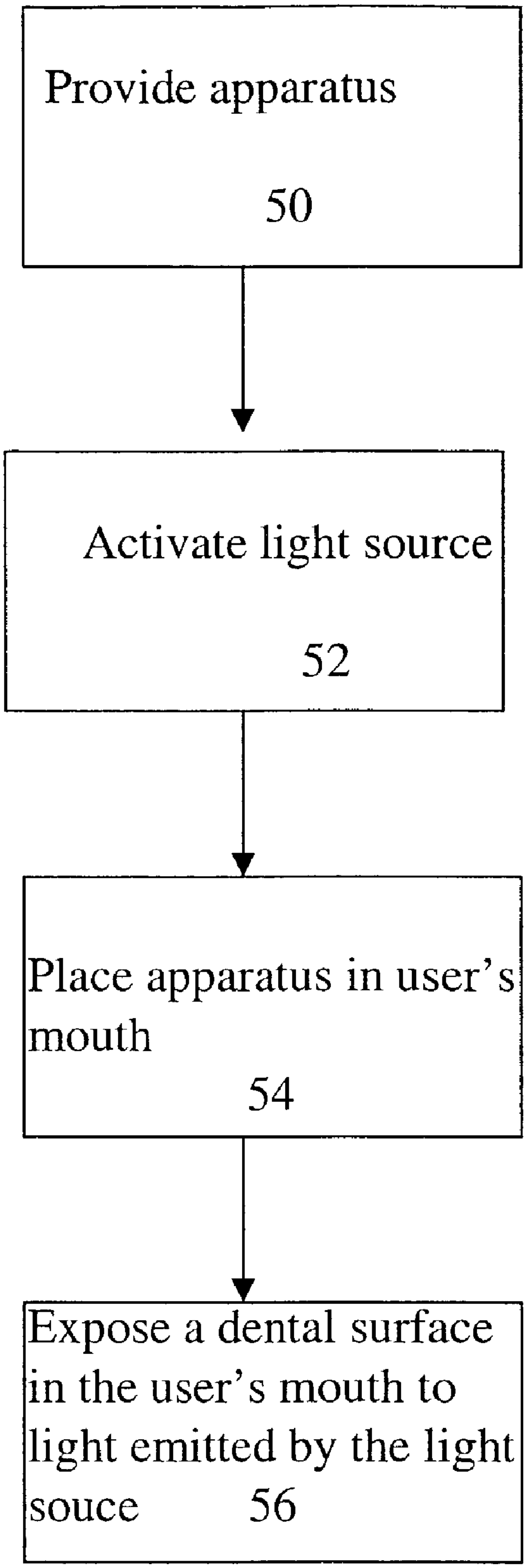
FIG. 4 is a flow diagram illustrating steps included in a method of bleaching a dental surface.
Figure 4B:
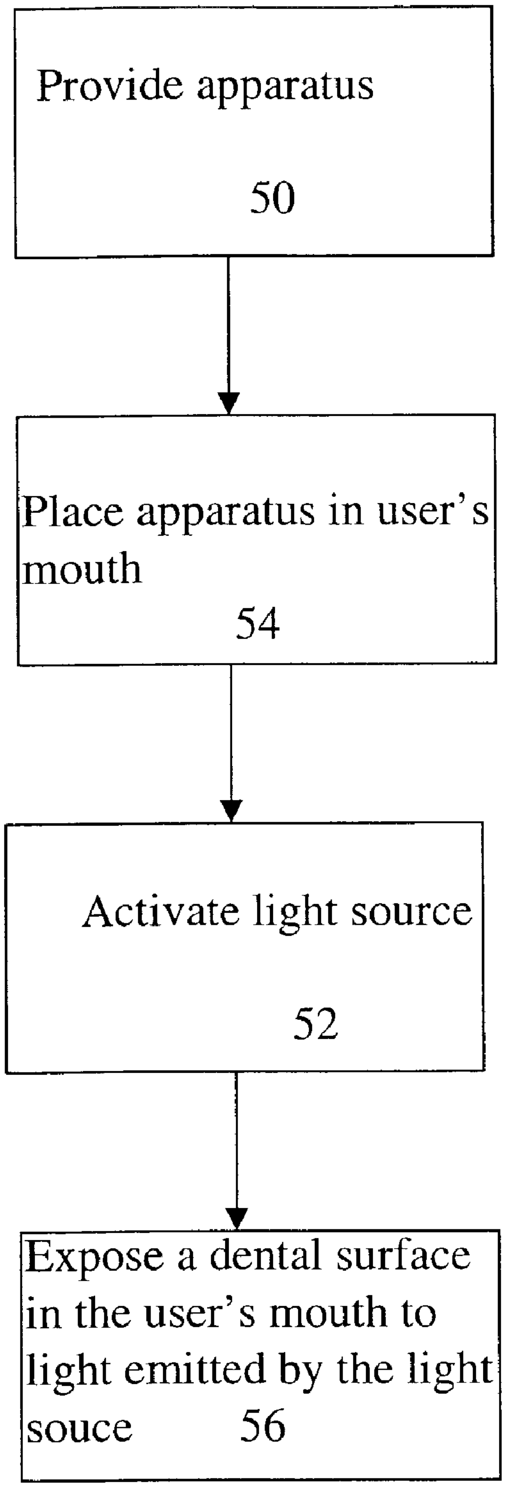

As illustrated in FIG. 4A, a method of treating a dental surface includes the step 50 of providing a dental apparatus wherein the apparatus includes a support structure, a dental whitening composition, and a light source. In another step 52 the light source included in the apparatus is activated such that light is emitted. Activation of the light source to emit light depends on the type of light source. For example, a diode may be activated by an on/off switch which in the "on" position makes an electrical connection between the diode and a power source. A phosphorescent or fluorescent source may be activated by exposure to exciting light of an appropriate wavelength for the phosphorescent material used. A chemiluminescent source is activated by mixing appropriate chemical reactants. In a further step 54 apparatus is placed entirely within the mouth of a patient using the apparatus such that the individual can close the mouth comfortably and no part of the apparatus remains outside the mouth. In a subsequent step 56, the dental surface is exposed to light emitted from dental apparatus, thereby treating the dental surface. As shown in FIG. 4B, step 52 wherein the light source is activated may be performed before or after step 54 wherein the apparatus is placed in the patient's mouth depending on comfort, convenience and safety considerations.

The dental surface is exposed to light emitted from dental apparatus for a period of time effective to whiten the dental surface. Typical exposure times range from 1 minute to 24 hours depending on the whitening composition used and the light source.

A user of an inventive apparatus or method is any mammal, typically a human.

While the inventive apparatus and method is described herein as including a support structure, it is appreciated that a whitening composition and illumination source may be applied to a dental surface to be treated without a support structure. For example, a luminescent compound and a whitening composition may be included together in a suitable form, such as a gel, liquid, putty, tape or gum which is applied directly to a dental surface to be treated.

EXAMPLE

Figure 5:
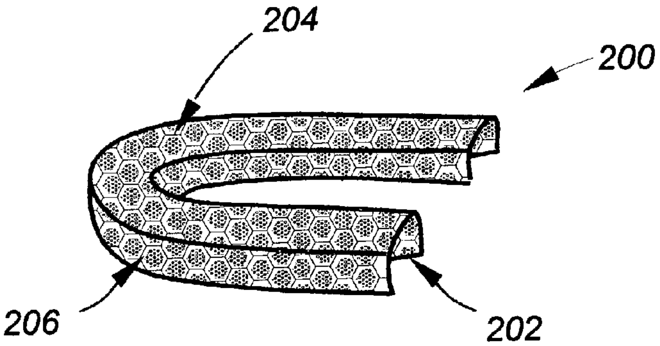
FIG. 5 is a drawing illustrating an embodiment of an inventive apparatus.

In one embodiment of an inventive apparatus, shown in FIG. 5, a support structure having a generally described U-shape is shown at 200. A textured surface 202 is shown including hexagonal cells 204. The cells 204 act as reservoirs for delivery of whitening compositions and here are shown containing beads 206 which enclose a whitening composition, such as hydrogen peroxide in a concentration ranging from 3-35%. A phosphorescent light source (not shown) is integral to the support shown, such that when an exciting light is directed at the support for a period of time, the support glows for a period after the exciting light is removed.

Although the invention is described as appropriate for delivering a dental whitening composition and for use in a method for whitening teeth, it is appreciated that a support structure as described herein may be used to deliver other treatments via an oral route. For example, therapeutic agents to treat dental or systemic diseases or conditions, such as anti-plaque agents, anesthetics, desensitizing agents, analgesics, antibiotics, antifungals, antimicrobials, antivirals, anti-inflammatory agents, remineralizing agents, anticarciogenic agents and steriods may be delivered using a support structure with or without an illumination source.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

I claim:

1. A dental apparatus, comprising:

a dental tray composed of a material that is moldable by hand at room temperature and customized by application to the dentition of a user and adapted to be placed entirely within a user's mouth;

a dental whitening composition in contact with the dental tray; and a light source disposed on or in the dental tray such that light emitted from the source impinges on the dental whitening composition, wherein the apparatus has a volume between 0.5-450 $cm^3$.

2. A method for treating a dental surface of a user, comprising the steps of:

(a) providing a dental apparatus comprising:

a moldable support structure dental tray composed of a material that is moldable by hand at room temperature;

a dental whitening composition in contact with the dental tray; and a light source disposed on or in the dental tray such that light emitted from the source impinges on the dental whitening composition, wherein the apparatus has a volume between 0.5-450 $cm^3$;

(b) activating the light source such that light is emitted by the light source;

(c) placing the apparatus entirely within the user's mouth;

(d) customizing the dental tray by manually molding it to the dentition of a user; and (e) exposing the dental surface to the light emitted by the light source, thereby treating the dental surface.

* * * * *